(12) United States Patent
Skjervold et al.

(10) Patent No.: US 7,618,652 B2
(45) Date of Patent: Nov. 17, 2009

(54) GLYCOSAMINOGLYCAN ANTICOAGULANTS DERIVED FROM FISH

(75) Inventors: Per Olav Skjervold, Ås (NO); Ole Rasmus Ødegaard, Ås (NO); Frank Brosstad, Ås (NO); Ragnar Flengsrud, Ås (NO)

(73) Assignee: Hepmarin AS, Ås (NO)

( * ) Notice: Subject to any disclaimer, the term of this patent is extended or adjusted under 35 U.S.C. 154(b) by 117 days.

(21) Appl. No.: 10/472,381

(22) PCT Filed: Mar. 22, 2002

(86) PCT No.: PCT/GB02/01397

§ 371 (c)(1), (2), (4) Date: Apr. 9, 2004

(87) PCT Pub. No.: WO02/076475

PCT Pub. Date: Oct. 3, 2002

(65) Prior Publication Data

US 2004/0171579 A1 Sep. 2, 2004

Related U.S. Application Data

(60) Provisional application No. 60/278,418, filed on Mar. 26, 2001.

(30) Foreign Application Priority Data

Mar. 23, 2001 (GB) .................................. 0107385.7

(51) Int. Cl.
*A61K 35/56* (2006.01)
*A61K 35/60* (2006.01)

(52) U.S. Cl. ........................ 424/520; 424/523; 424/550; 424/572

(58) Field of Classification Search .................. 424/523, 424/550, 572, 520
See application file for complete search history.

(56) References Cited

U.S. PATENT DOCUMENTS

| | | | |
|---|---|---|---|
| 4,230,699 A | 10/1980 | Fussi et al. | |
| 4,438,108 A | 3/1984 | Sanders et al. | |
| 4,446,126 A * | 5/1984 | Jordan | 514/56 |
| 4,533,549 A | 8/1985 | Lasker | |
| 4,987,222 A | 1/1991 | De Ambrosi et al. | |
| 6,342,367 B1 | 1/2002 | Sumi et al. | |
| 6,491,965 B1 * | 12/2002 | Berry et al. | 427/2.1 |
| 2001/0036924 A1 * | 11/2001 | Weidner | 514/42 |
| 2007/0155652 A1 * | 7/2007 | Takigawa et al. | 514/2 |
| 2007/0160979 A1 * | 7/2007 | Andersson | 435/5 |

FOREIGN PATENT DOCUMENTS

| | | |
|---|---|---|
| EP | 0 475 383 | 3/1992 |
| EP | 0 509 517 | 10/1992 |
| EP | 0 940 410 | 9/1999 |
| IT | 1 269 189 | 3/1997 |
| JP | 63010601 A * | 1/1988 |
| JP | 02270823 A * | 11/1990 |
| WO | WO 01 64756 | 9/2001 |

OTHER PUBLICATIONS

Purificacion B. Gomes et al., "Distribution of Heparin and Other Sulfated Glycosaminoglycans in Vertebrates", Coomp. Biochem. Physiol., 1982, 73B(4):857-863.
Peter Hovingh et al., "Biological implications of the structural, antithrombin affinity and anticoagulant activity relationships among vertebrate heparins and heparan sulphates", Biochem. J., 1986, 237:573-581.
S.Z. Qasim et al., "Occurrence of heparin in the Blood of Fish and its Prevention of the Clotting of Fish Plasma", Nature, 1961, 189:764-765.
Catherine Veil et al., "Sur la presence d'heparine dans les ecailles de Cyprinus carpio", Seances Soc. Biol. Fil, 1950, 144(21-22):1483-1484.
Ganesh Venkataraman et al., "Sequencing Complex Polysaccharides", Science, 1999, 286: 537-542.
John W. Eikelboom et al., "Low molecular weight heparins and heparinoids", The Medical Journal of Australia, 2002, 177(6): 379-383.
Jeffrey I. Weitz, M.D., "Low-Molecular-Weight Heparins", The New England Journal of Medicine, 1997, 337(10): 688-698.
Guilherme F. Medeiros et al., "Distribution of sulfated glycosaminoglycans in the animal kingdom: widespread occurrence of heparin-like compounds in invertebrates", Biochimica et Biophysica Acta, 2000, 1475: 287-294.
Barbara Mulloy et al., "Order out of complexity- protein structures that interact with heparin", Current Opinion in Structural Biology, 2001, 11: 623-628.
Matthew A. Nugent, "Heparin sequenceing brings structure to the funcction of complex oligosaccharides", PNAS, 2000, 97(19): 10301-10303.
Gunnar Pejler et al., "Structure and Antithrombin-binding Properties of Heparin Isolated from the Clams *Anomalocardia brasiliana* and *Tivela mactroides*", The Journal of Biological Chemistry, 1987, 262(24): 11413-11421.
C.A.A. van Boeckel et al., "Glycosaminoglycans: Synthetic fragments and their interaction with serine protease inhibitors", Pure & Appl. Chem., 1995, 67(10): 1663-1672.
Nadar et al, *Brazilian J. of Med. and Biolog. Res.*, 34(3):699-709, (2001).
Chavante et al, *International J. of Biological Macromolecules*, 27:49-57 (2000).
Dietrich et al, *Biochemica et Biophysica Acta*, 1428:273-283 (1999).
Vivés et al, *Biochem. J.*, 339:767-773 (1999).

* cited by examiner

*Primary Examiner*—Ruth A Davis
(74) *Attorney, Agent, or Firm*—Sughrue Mion, PLLC

(57) ABSTRACT

The present invention provides anticoagulant piscine gill glucosaminoglycans, high affinity anticoagulant piscine glycosaminoglycans anticoagulant glycosaminoglycans extractable from salmon guts, skin, tail or gills and salts and derivatives thereof.

15 Claims, 4 Drawing Sheets

GLYCOSAMINOGLYCAN ANTICOAGULANTS DERIVED FROM FISH

This Application is a 371 of PCT/GB02/01397, filed Mar. 22, 2002; which is a Continuation-In-Part of U.S. Provisional Application No. 60/278,418, filed Mar. 26, 2001; the disclosure of each of which is incorporated herein by reference.

The present invention relates to anticoagulant piscine glucosaminoglycans, compositions containing anticoagulant piscine glucosaminoglycans, equipment coated with anticoagulant piscine glucosaminoglycans, preparation of anticoagulant piscine glucosaminoglycans, uses of anticoagulant piscine glucosaminoglycans and methods of treatment with anticoagulant piscine glucosaminoglycans.

Glycosaminoglycans consist of two sub-groups namely, galactosaminoglycans and glucosaminoglycans.

Heparin is the name given to a class of sulphated glucosaminoglycans having anticoagulant properties. Heparin is widely used medically both as a coating agent for invasive medical equipment, e.g. catheters and implants, and as a therapeutic or prophylactic agent. Besides heparin, other anticoagulant sulphated glucosaminoglycans (often referred to as heparinoids) are known, e.g. heparan sulphate. These too have been used to achieve anti-coagulant or anti-opsonization effects. However heparin is the most commercially significant of the group.

The anticoagulant glucosaminoglycans are polysaccharides with repeating sulphated disaccharide units. The polysaccharide structure may additionally contain other oligosaccharide substructures, e.g. the pentasaccharide unit known to bind to antithrombin (see Casu et al., Seminars in Thrombosis and Hemostasis 25 (Suppl. 3): 17-25 (1999) and Lindahl et al., J. Biol. Chem. 258: 9826-9830 (1983)). Thus besides its trisulphated disaccharide repeat unit, heparin contains additional saccharide units, e.g. disulphated disaccharides, and some heparin contains the pentasaccharide which is a high affinity binding site for antithrombin. Heparin containing this pentasaccharide binding site for antithrombin is known as high affinity heparin.

The different glucosaminoglycans differ in the inter-saccharide bonds and the saccharide ring substitution. Moreover for a particular animal species the chain length varies and thus the glucosaminoglycans have molecular weight distributions rather than specific molecular weights, i.e. they are polydisperse.

Currently, mammalian tissue, especially from pigs, oxen and sheep, is the source for heparin. The isolation and purification of heparin from mammalian tissue is described for example in U.S. Pat. Nos. 2,884,358, 2,989,438, 3,016,331, Roden et al., Methods Enzymol. 26: 73 (1972), U.S. Pat. Nos. 4,119,774, 4,122,250 and WO99/03893 and in the 1979 patent publications of Pharmacia and Kabi.

Besides natural heparins, there has recently been much interest in the so-called low molecular weight heparins (LMWHs). These are salts of sulphated glucosaminoglycans having an average molecular weight below 8 kD with at least 60% mol. having a molecular weight below 8 kD. These are prepared by fractionation or depolymerization of natural mammalian heparin which typically may have molecular weights in the range 5 to 40 kD. Commercially available LMWHs include for example salts of ardeparin, certoparin, enoxaparin, nadroparin, parnaparin, reviparin, dalteparin and tinzaparin. (See Linhardt et al., Seminars in Thrombosis and Hemostasis 25 (Suppl. 3): 5-16 (1999)).

Mammalian derived natural products however have several drawbacks for use with humans, especially where, as with heparins and heparinoids, the use involves invasive administration, e.g injection, insertion into tissue or blood vessels, or application during surgery. In particular there is concern that mammalian derived natural products may be contaminated with infectious agents such as bacteria, viruses and prion proteins.

We have now surprisingly found that glucosaminoglycans having excellent anticoagulant properties can be extracted from fish gills and that accordingly anticoagulant glucosaminoglycans for medical use may be isolated from fish gills.

Viewed from one aspect therefore the present invention provides anticoagulant piscine gill glucosaminoglycan and salts and derivatives, especially physiologically tolerable derivatives, thereof, preferably in cell-free form, also preferably in sterile form, more preferably in at least substantially pure form (e.g. containing no more than 10% by weight, preferably no more than 2% wt, of non-glucosaminoglycan biological materials). By biological materials is meant carbon-containing materials naturally present in the fish and having a molecular weight in excess of 500 D. Typically the glucosaminoglycan will have a molecular weight in the range of 500 to 30,000 Daltons, preferably at least 1000 Daltons, particularly preferably at least 1500 Daltons.

Viewed from a further aspect the invention provides a method of producing anticoagulant glycosaminoglycan comprising extracting endogenous anticoagulant glycosaminoglycan from animal material and optionally depolymerizing and/or molecular weight fractionating said endogenous anticoagulant glycosaminoglycan, characterised in that the animal material is fish gill material.

The production of anticoagulant high affinity glycosaminoglycans, in particular glucosaminoglycans, from fish (i.e. fin fish), especially salmon, is also novel and inventive and forms a further aspect of the invention. Not all glucosaminoglycans or even glycosaminoglycans have the pentasaccharide binding site for antithrombin; indeed generally less than half do have such sites. Thus viewed from this aspect the invention provides high affinity anticoagulant piscine glycosaminoglycan (i.e. having the pentasaccharide antithrombin binding site), especially anticoagulant glucosaminoglycans, and salts and high affinity derivatives thereof.

Viewed from a further aspect the invention provides a method of producing high affinity anticoagulant glycosaminoglycan comprising extracting endogenous anticoagulant glycosaminoglycan from animal material and optionally depolymerizing and/or molecular weight fractionating said endogenous anticoagulant glycosaminoglycan, characterised in that the animal material is fish material.

The production of anticoagulant glycosaminoglycans, especially glucosaminoglycans, from salmon guts, skin, gills and tail (especially guts and gills, in particular gills) is also novel and forms a further aspect of the invention. Such anticoagulant glycosaminoglycans, especially high affinity glucosaminoglycans, have particularly good anticoagulant properties. Thus viewed from a further aspect the invention provides anticoagulant glycosaminoglycans, and salts and derivatives thereof, extractable from salmon guts, skin, gills or tail, especially guts or gills.

Viewed from a further aspect the invention provides a method of producing anticoagulant glycosaminoglycan comprising extracting endogenous anticoagulant glycosaminoglycan from animal material and optionally depolymerizing and/or molecular weight fractionating said endogenous anticoagulant glycosaminoglycan, characterised in that the animal material is salmon guts, skin, gills or tail, especially guts or gills.

Viewed from a further aspect the invention provides a pharmaceutical composition comprising anticoagulant piscine glycosaminoglycan according to the invention or a salt or derivative thereof together with a physiologically tolerable carrier or excipient, and optionally also a therapeutic or prophylactic drug substance.

Viewed from a still further aspect the invention provides medical apparatus, e.g. a catheter, stent or implant, having a surface coated at least in part with anticoagulant piscine glycosaminoglycan according to the invention or a salt or derivative thereof.

Viewed from a still further aspect the invention provides the use of anticoagulant piscine glycosaminoglycan according to the invention or a salt or derivative thereof in mammalian, especially human, medical treatment.

Viewed from another aspect the invention provides anticoagulant piscine glycosaminoglycan according to the invention or a salt or derivative thereof for use in mammalian medical treatment.

Viewed from yet another aspect the invention provides a method of treatment of a human or mammalian body which method comprises administering or introducing into said body an anticoagulant effective amount of anticoagulant piscine glycosaminoglycan according to the invention or a salt or derivative thereof.

The extraction, purification and if desired depolymerization and molecular weight fractionation of anticoagulant piscine glycosaminoglycan from fish material may be effected analogously to the extraction, purification, etc. of heparin and heparinoids from mammalian sources, e.g. as described in the publications mentioned above. If desired, the fish material used for extraction of glycosaminoglycans may be subjected to physical or chemical pretreatment, e.g. maceration, acid or base treatment, etc.

The anticoagulant glycosaminoglycan (anticoagulant GAG) of or used in the invention may be a heparin, a heparinoid, or a low molecular weight heparin or heparinoid, or a mixture of two or more thereof. Preferably it is a sulphated GAG, in particular a heparin or LMWH, especially preferably it contains at least one pentasaccharide unit having the sequence:
N-acetylglucosamine-6-O-sulphate,
glucaronic acid,
N-sulphated glucosamine-3,6-O-disulphate,
iduronic acid 2-O-sulphate and
N-sulphated glucosamine-6-O-sulphate,
i.e. it is especially preferably a high affinity GAG.

By "anticoagulant" it is meant that the GAG has the ability to bind to antithrombin, an inter-alpha-trypsin inhibitor, factor Xa, and other proteins to which mammalian heparin binds, e.g. immobilized on a substrate such as a gel matrix, and/or the ability to delay or prevent clotting in human plasma (e.g. increasing clotting time by at least 10% in the test of Example 5 when the GAG is added at 1.0 mg/mL plasma) or to prolong bleeding in a mammal (e.g. a mouse).

The fish from which the fish material from which the piscine GAG is extracted may be any fish; however fish used as food sources for mammals or as raw materials for fish meal, fish food, and fish oil are preferred. Particularly preferably farmed fish are used. Examples of suitable fish include: carp, barbell and other cyprinids; cod, hake, haddock; flounder, halibut, sole; herring, sardine, anchovy; jack, mullet, saury; mackerel, snoek, cutlass fish; red fish; bass; eels (e.g. river eels, conger, etc.); salmon, cod, trout; shad; shark; ray; sturgeon; paddle fish; tilapia and other cichlids; tuna, bonito, bill fishes; diadromous fish; etc. Particular examples of suitable fish include: flounder, halibut, sole, cod, hake, haddock, bass, jack, mullet, saury, herring, sardine, anchovy, tuna, bonito, bill fish, mackerel, snoek, shark, ray, capelin, sprat, brisling, bream, ling, wolf fish, salmon, trout, coho and chinock. Especially preferably the fish used is trout, salmon, cod or herring, more especially salmon.

The piscine GAG may be used according to the invention in its naturally occurring form following extraction. However alternatively it may be converted into salt form, preferably with a physiologically tolerable counterion (e.g. sodium, calcium, magnesium, potassium, ammonium or meglumine), or derivatised, e.g. to facilitate its binding to a surface of an item of medical apparatus, or molecular weight fractionated or depolymerized (e.g. to produce a GAG fraction meeting the molecular weight definition for LMWH). Such derivatives are likewise preferably physiologically tolerable. Conventional chemical reactions may be used for such derivatization or depolymerization, e.g. reactions with coupling agents or with molecular weight reducing agents as described in Linhardt et al. supra. Examples of particular depolymerization techniques include: cleavage with nitrous acid at pH 1.5; periodate oxidation followed by cleavage with dilute alkali or mild acid; de-N-acetylation and treatment with nitrous acid at pH 4; and activation with carbodiimide, hydrazine, aminomethylsulphonate or other carboxyl activating agents followed by treatment with dilute alkali.

Coating of items of medical apparatus with piscine GAG may be effected analogously to coating with mammalian heparin.

Piscine GAG is chemically distinct from mammalian heparin as demonstrated by the nmr spectra in FIGS. 1 to 4 of the accompanying drawings. FIGS. 1 and 2 are respectively nmr spectra of pig and bovine heparin. FIGS. 3 and 4 are nmr spectra of salmon GAG from intestines and gills respectively. As can be seen, the piscine GAG shows peaks at 2.70-2.95 and 3.935 to 3.960 ppm respectively. Viewed from a further aspect therefore the invention provides GAG having a peak at 2.70 to 2.95 ppm in its $^1$H-nmr spectrum in $D_2O$ at 300 MHz and 28° C., in particular a peak which is at least 10% of the intensity of any peak in the 2.95 to 3.15 ppm region. Viewed from a further aspect the invention also provides GAG having a peak at 3.935 to 3.960 ppm in its $^1$H-nmr spectrum in $D_2O$ at 300 MHz and 28° C., in particular a peak which is more intense than any peak in the 3.960 to 4.100 ppm range. By its spectrum is here meant the spectrum of the GAG after affinity purification on an antithrombin-sepharose column (see Example 1 hereinafter).

The piscine GAGs may be separated from mixtures by sequential precipitation in various organic solvents (e.g. acetone, methanol, ethanol) or by electrophoretic separation. Alternatively, the GAG groups may be separated on anion exchangers (see N. Volpi, J. Chromatography B 684:27-34 (1996); Analytical Biochem 240:114-118 (1996); J. Chromatography 622:13-20 (1993); Analytical Biochem 218:382-391 (1994)).

The GAG compositions according to the invention may contain non-GAG components conventional in mammalian GAG compositions, e.g. water (preferably water for injections), ethanol, buffers, osmolality adjusting agents, preservatives, etc.

Piscine GAGs may be used in substantially the same quantities as mammalian GAGs are conventionally used or at lower doses as a result of its anticoagulant efficacy.

Besides use as anticoagulants, the piscine GAGs of the invention may be used as antithrombotics, anti-atherosclerotics, complement inhibitors, anti-inflammatories, anti-cancer agents, anti-viral agents, anti-dementia agents (e.g. anti-Alzheimer agents), anti-prion agents, anti-parasitics, opsonization inhibitors, biomaterials, angiogenesis regulators, and in the treatment of vascular deficit, wounds and immune response disorders (e.g. AIDS), etc. They may be administered enterally or parenterally, e.g. orally or subcutaneously or bound to an object or drug material placed into tissue or the circulatory system.

Besides such therapeutic and surgical uses, the piscine GAGs of the invention may be used for diagnostic purposes, e.g. diagnostics assays, and non-medical uses for which heparin is suited or currently used. Thus viewed from a further aspect the invention provides a diagnostic assay kit comprising an anticoagulant, characterised in that said anticoagulant is a piscine glycosaminoglycan according to the invention.

The invention extends to piscine GAGs which are not anticoagulants, and their uses, e.g. for purposes for which non-anticoagulant mammalian GAGs are suitable. Fareel et al. in Recent Advances in Blood Coagulation, pages 169-187 (Ed. Poller) have stated that GAGs, to be useful as antithrombotics, need not necessarily be anticoagulants or react with antithrombin.

Documents referred to herein are hereby incorporated by reference.

Figure 1:
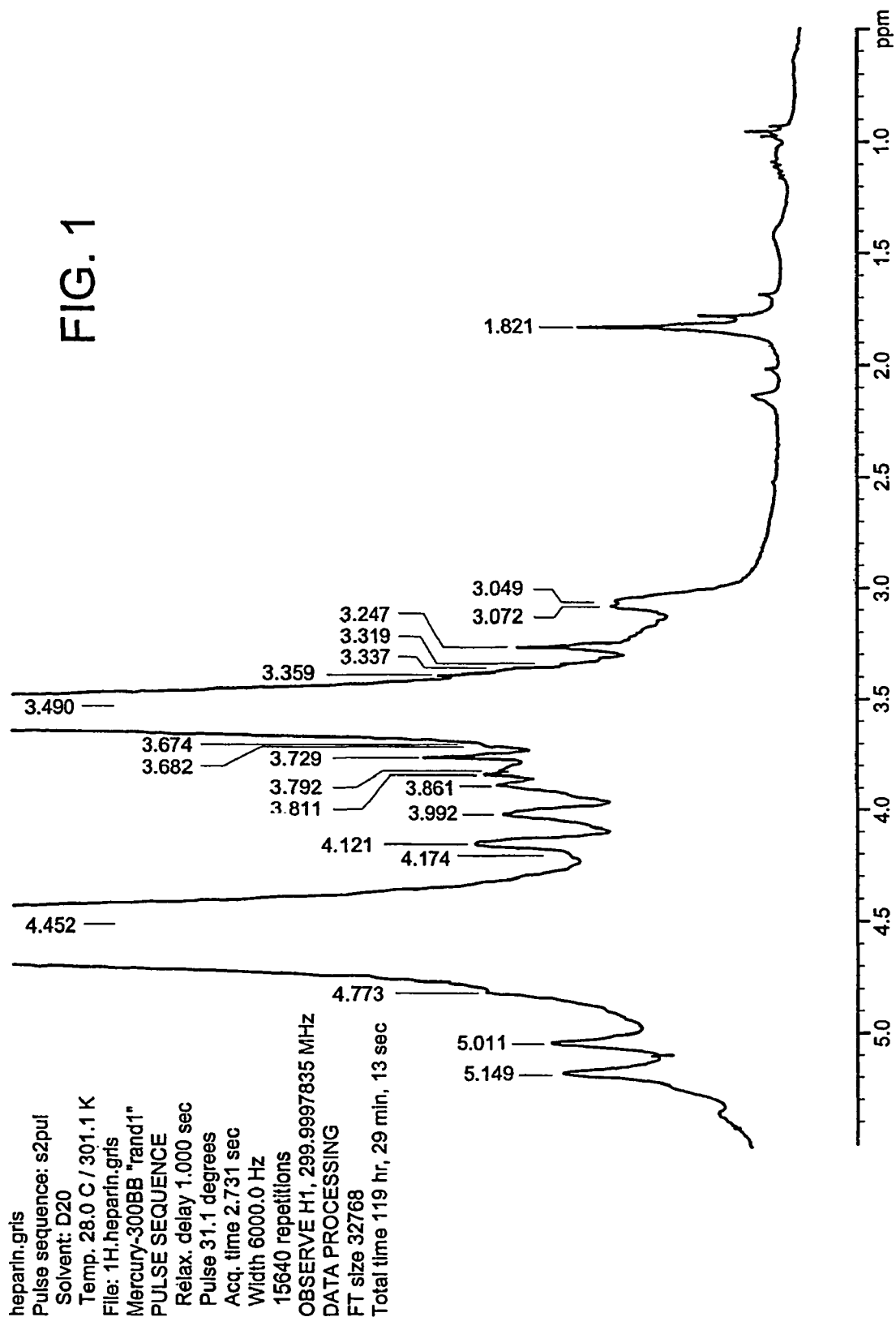
FIG. 1 shows the nmr spectra of pig heparin. The nmr spectra of pig heparin demonstrates that piscine GAG, as shown in FIGS. 3 and 4, is chemically distinct from mammalian heparin.

The present invention will now be illustrated further by the following non-limiting Examples.

EXAMPLE 1

Extraction of Salmon GAG

Salmon were slaughtered and the intestines were removed and kept cold (ca. −5 to +5° C.) until the following day when they were frozen to −80° C.

100 g of the frozen intestines were thawed in 100 mL Tris buffer (0.05M Tris/HCl/0.15M NaCl, pH 7.5) and homogenized in an Ultra Turrax® tissue grinder. The homogenizate was incubated at 80° C. for 1 hour in a water bath, cooled to ambient temperature and centrifuged for 30 minutes at 12000 rpm. The supernatant was removed and the residue was homogenized again in 25 mL of 4M guanidine.HCl in the same buffer. This was again centrifuged as above and the supernatant was removed and combined with the earlier supernatant. The combined supernatant was dialyzed against 2×2L of Tris buffer (0.025M Tris/HCl/0.15M NaCl, pH 7.5) and centrifuged again as above. Using the Tris buffer used for the dialysis, the resultant supernatant was applied to a column (20 mL bed volume)of cyanogen bromide activated Sepharose 4B (from Pharmacia) to which human anti-thrombin was coupled according to the manufacturers' instructions. The same buffer was used to wash the column and subsequently salmon GAG was eluted using the same buffer at about 0.5 mL/min with a linear gradient of salt concentration rising from 0.15M to 2.15M NaCl.

Samples of fractions from the elution were subjected to a carbazole test for heparin and those fractions testing positive were combined, dialyzed against 5 mM $NH_4HCO_3$ using a 3500 D mol. wt cut-off membrane, and freeze dried.

EXAMPLE 2

Extraction of Salmon GAG

Using the same procedure as Example 1, salmon GAG was extracted from 40 g of frozen salmon gills. In the initial incubation, 50 mL rather than 100 mL of extraction buffer was used.

EXAMPLE 3

Antithrombin Binding 2.5 mg of the freeze-dried GAG of Example 1 was dissolved per 1 mL of a test buffer (comprising Tris buffer (0.05M Tris/2 mM $Na_2EDTA$/0.18M NaCl), 10 g/L PEG 6000, 0.1 mL/L Tween 80 and HCl to pH 8.4) to produce a buffered test sample. 0.2 mL of the test buffer alone (Run 1), or 0.1 mL of the test buffer with 0.1 mL of 3 U/mL mammalian heparin (Run 2), or 0.1 mL of the test buffer and 0.1 mL of the test sample (Run 3) were mixed with 0.1 mL bovine thrombin (5U/mL in the test buffer) and 0.1 mL antithrombin (1500 IU/Ky—Kybernin from Kabi—10 mg/mL in the test buffer), incubated at 37° C. for 5 minutes, mixed with 0.1 mL synthetic substrate (S-2238 from Kabi—0.75 mmol/L in water), and incubated at 37° C. for a further 2 minutes. The reaction was stopped by adding 0.1 mL of 50% acetic acid and the amidolytic activity on the substrate was measured by determining the absorbance (A) at 405 nm.

| Run | A | |
|---|---|---|
| 1 | 0.636 | (no GAG) |
| 2 | 0.062 | (mammalian GAG) |
| 3 | 0.228 | (piscine GAG) |

The test was repeated with 0, 5 and 20 minutes incubation at 37° C. before synthetic substrate addition. In Runs 4 to 6, 0.6 mL test buffer were added to 0.3 mL thrombin and 0.3 mL antithrombin, and incubated at 37° C. with 0.4 mL samples being extracted after 0, 5 and 20 minutes. The extracts were added to 0.1 mL substrate, incubated at 37° C. for 2 minutes, the reaction was stopped and absorbance at 405 nm was measured. In Runs 7 to 9, 0.3 mL test buffer, 0.3 mL antithrombin, 0.3 mL thrombin and 0.3 mL heparin were mixed before the first incubation/extraction and in Runs 10 to 12 0.3 mL test buffer, 0.3 mL antithrombin, 0.3 mL thrombin and 0.3 mL test sample were mixed before the first incubation/extraction.

| Run | 1st Incubation Time (min) | A* |
|---|---|---|
| 4 | 0 | 1.031 (no GAG) |
| 5 | 5 | 0.970 (no GAG) |
| 6 | 20 | 0.287 (no GAG) |
| 7 | 0 | 0.202 (mammalian GAG) |
| 8 | 5 | 0.086 (mammalian GAG) |
| 9 | 20 | 0.213 (mammalian GAG) |
| 10 | 0 | 1.058 (piscine GAG) |
| 11 | 5 | 0.221 (piscine GAG) |
| 12 | 20 | 0.139 (piscine GAG) |

*average of two results.

Runs 1 to 3 were repeated (as Runs 13 to 15) using the piscine GAG of Example 2.

| Run | A | |
|---|---|---|
| 13 | 0.852 | (no GAG) |
| 14 | 0.070 | (mammalian GAG) |
| 15 | 0.268 | (piscine GAG) |

EXAMPLE 4

Clotting Tests

The piscine GAG of Example 1 was tested for its ability to delay or prevent clotting in human plasma. 2 mg of the freeze dried material was dissolved in 0.5 mL 0.05M Tris/HCl/0.1M NaCl buffer, pH 7.4 to give a 4 mg/mL concentration. This was further diluted to give 0.400, 0.200, 0.133, 0.080, 0.067 and 0.040 mg/ML samples. 100 μL of each of these was mixed with 100 μL plasma and 100 μL 3 U/mL bovine thrombin and the time to clotting was measured. As a control (0 mg/mL), 100 μL of the buffer was used.

| Concentration (mg/mL) | Time* (sec.) |
|---|---|
| 0 | 20.2 |
| 0.040 | 22.8 |
| 0.067 | 25.5 |
| 0.080 | 29.3 |
| 0.133 | 46.8 |
| 0.200 | >120 |
| 0.400 | >450 |

*average of 4 results

EXAMPLE 5

Clotting Test

Using the Cephotest (Nycomed, Oslo) on a StaCompact (Stago, France) apparatus the effect of the piscine GAG of Example 1 on plasma clotting time was measured.

Piscine GAG of Example 1 was dissolved in Owren-Koller buffer to concentrations of 0.08 to 10.0 mg/mL. These were diluted in a 9:1 volume ratio with pooled human plasma and the clotting times determined.

| Piscine GAG concentration (mg/mL) | Clotting Time (seconds) |
|---|---|
| 0 | 28.1 |
| 0.008 | 28.5 |
| 0.016 | 29.8 |
| 0.033 | 31.4 |
| 0.067 | 34.1 |
| 0.125 | 41.6 |
| 0.250 | 58.4 |
| 0.500 | 96.9 |
| 0.750 | 134.9 |
| 1.000 | 178.7 |

EXAMPLE 6

Activity in Heparin Test 6 mg of the piscine GAG of Example 1 was dissolved in 0.6 mL Owren Koller buffer to give a 10 mg/mL primary solution. Samples of this were diluted with Owren Koller buffer (from Stago, France) to give 5 mg/mL, 2.5 mg/mL, 1.25 mg/mL, 0.67 mg/mL, 0.33 mg/mL, 0.16 mg/mL and 0.08 mg/mL secondary samples. These were tested for their "heparin activity" using a standard Stachrom LMWH kit from Stachrom. Since the test system involves addition of test sample and antithrombin to plasma, the results are independent of the antithrombin content of the plasma. The 'heparin' content of the piscine GAG was determined in U/mL relative to standard heparin samples (Hepanorm from Stago), giving an average value of "heparin activity" U/mg for the piscine GAG as anti Xa of 1.39.

EXAMPLE 7

NMR-Spectra of GAGs

Bovine heparin and porcine heparin (sodium salts, H-0777 and H-9399 from Sigma—isolated from intestinal mucosa) were purified using an antithrombin-Sepharose column as in Example 1.

Figure 2:
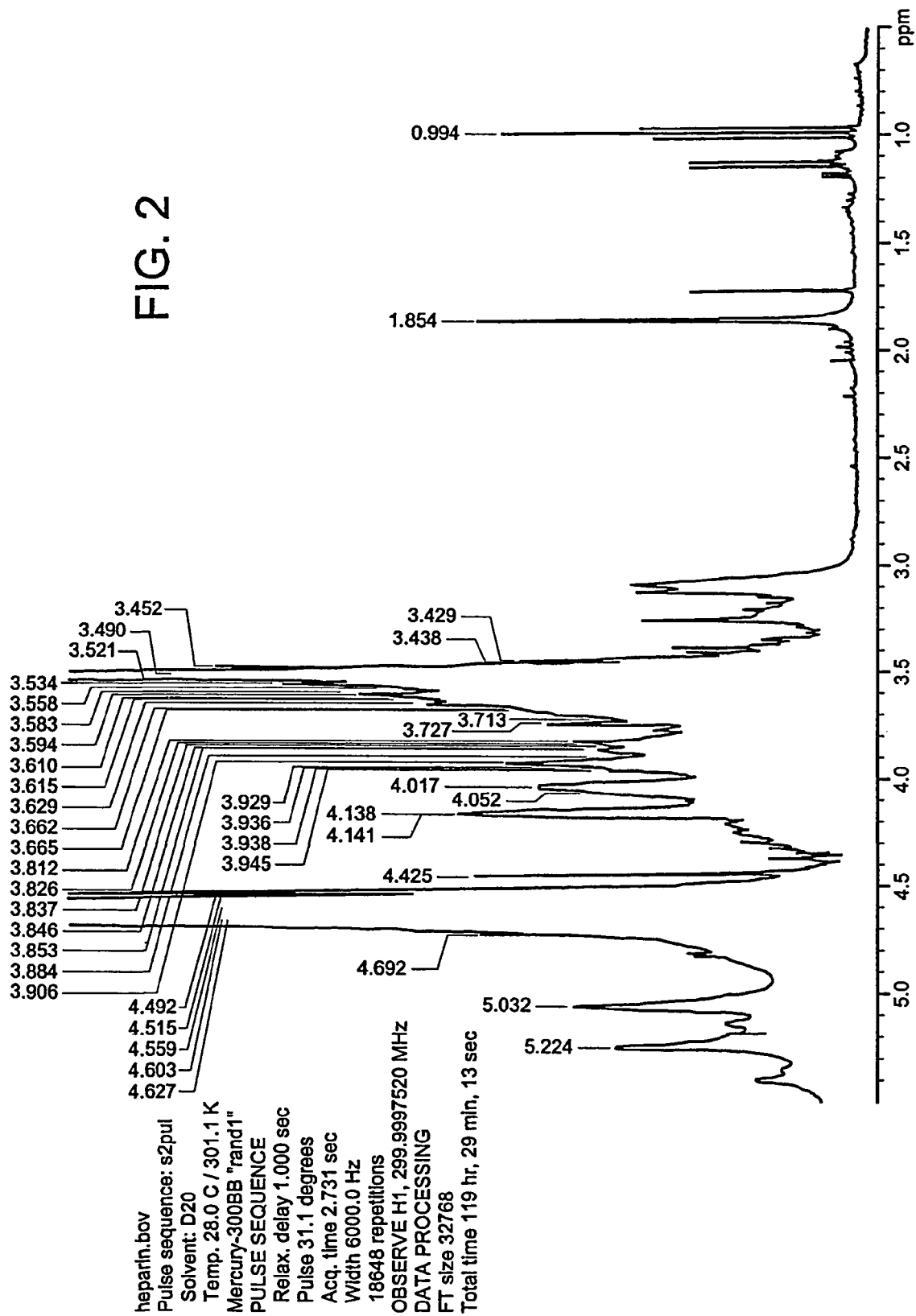
FIG. 2 shows the nmr spectra of bovine heparin. The nmr spectra of bovine heparin demonstrates that piscine GAG, as shown in FIGS. 3 and 4, is chemically distinct from mammalian heparin.
Figure 3:
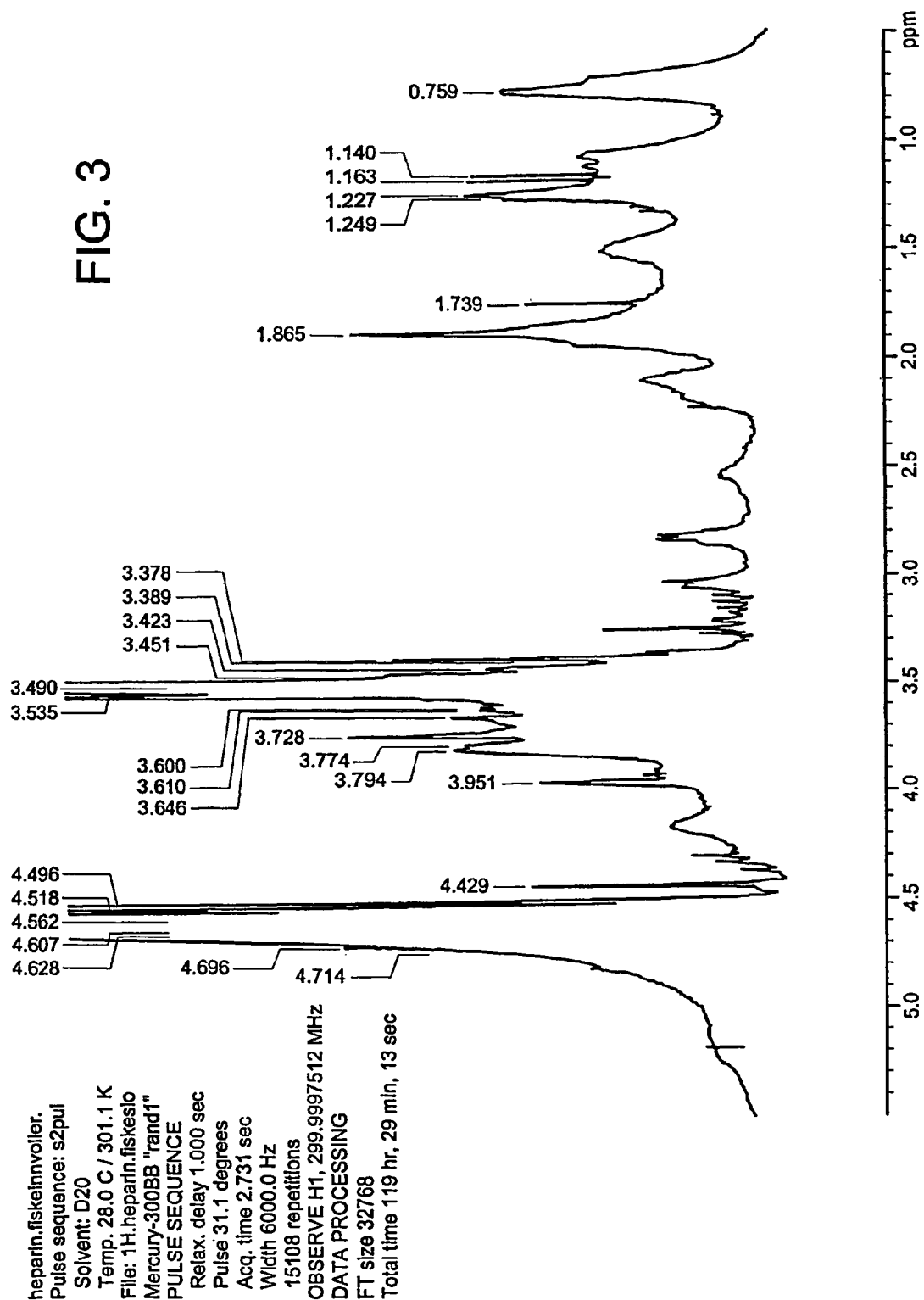
FIG. 3 shows the nmr spectra of salmon GAG from intestines.
Figure 4:
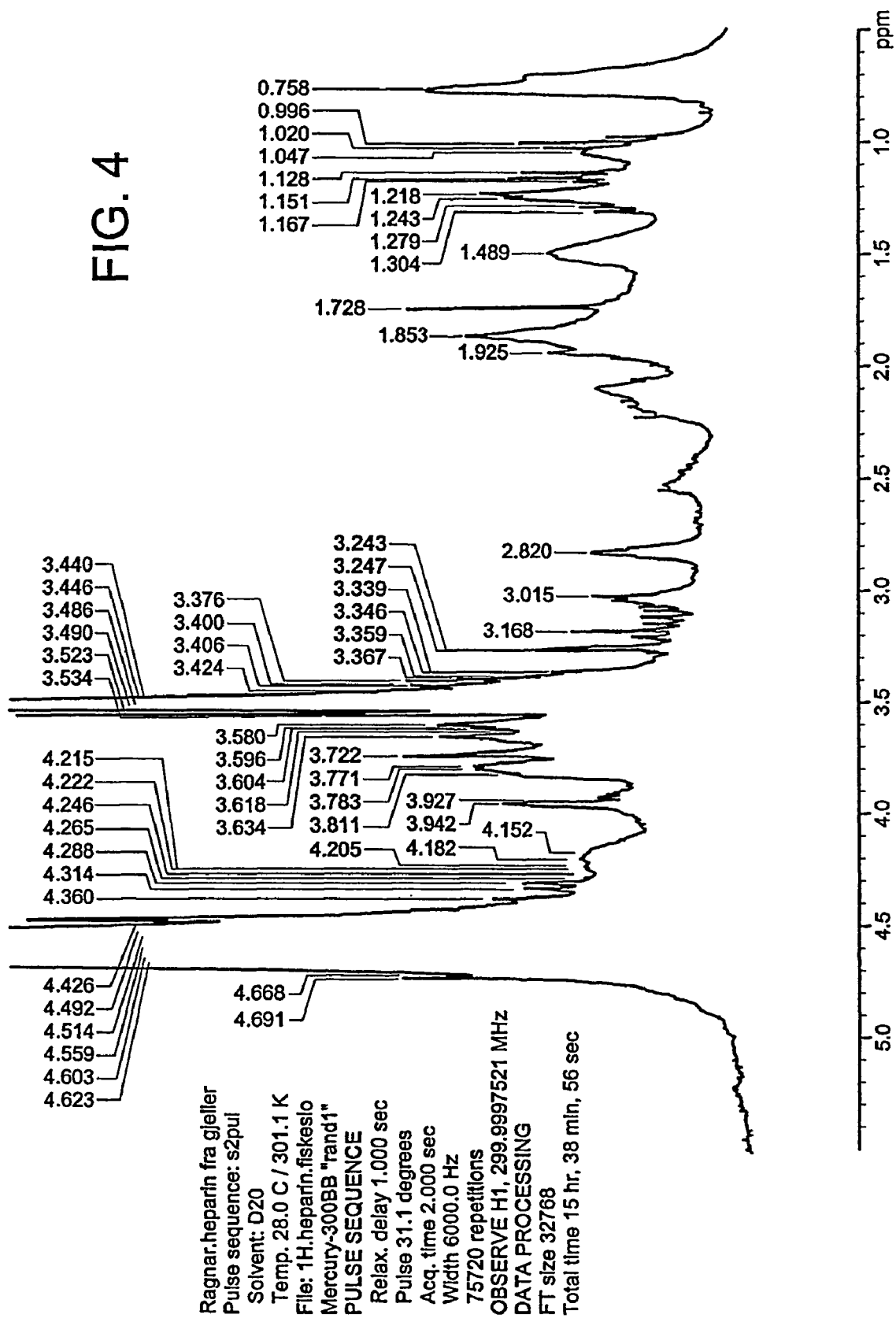
FIG. 4 shows the nmr spectra of salmon GAG from gills.

Virtually salt free samples of the purified bovine and porcine heparins and the salmon GAG of Examples 1 and 2 were freeze-dried and dissolved in $D_2O$. Tris was added as a marker. The $^1H$-nmr spectra were then recorded at 28° C. using a Varian 300 MHz nmr spectrometer. The spectra are shown in FIGS. 1 to 4. In these the major peaks at 4.65 and 3.5 ppm are water and Tris respectively.

Recorded peaks are set out in Table 1 below.

TABLE 1

| Sample | Peaks (ppm) | | | | |
|---|---|---|---|---|---|
| Bovine | 0.994 | 1.854 | 3.429 | 3.438 | 3.452 |
| | 3.490 | 3.521 | 3.534 | 3.558 | 3.583 |
| | 3.594 | 3.610 | 3.615 | 3.629 | 3.662 |
| | 3.665 | 3.713 | 3.727 | 3.812 | 3.826 |
| | 3.837 | 3.846 | 3.853 | 3.884 | 3.906 |
| | 3.929 | 3.936 | 3.938 | 3.945 | 4.017 |
| | 4.052 | 4.138 | 4.141 | 4.425 | 4.492 |
| | 4.515 | 4.559 | 4.603 | 4.627 | 4.692 |
| | 5.032 | 5.224 | | | |
| Porcine | 1.821 | 3.049 | 3.072 | 3.247 | 3.319 |
| | 3.337 | 3.359 | 3.490 | 3.674 | 3.682 |
| | 3.729 | 3.792 | 3.811 | 3.861 | 3.992 |
| | 4.121 | 4.174 | 4.452 | 4.773 | 5.011 |
| | 5.149 | | | | |
| Salmon intestine | 0.759 | 1.140 | 1.163 | 1.227 | 1.249 |
| | 1.739 | 1.865 | 3.378 | 3.389 | 3.423 |
| | 3.451 | 3.490 | 3.535 | 3.600 | 3.610 |
| | 3.646 | 3.728 | 3.774 | 3.794 | 3.951 |
| | 4.429 | 4.496 | 4.518 | 4.562 | 4.607 |
| | 4.628 | 4.696 | 4.714 | | |
| Salmon gills | 0.758 | 0.996 | 1.020 | 1.047 | 1.128 |
| | 1.151 | 1.167 | 1.218 | 1.243 | 1.279 |
| | 1.304 | 1.489 | 1.728 | 1.853 | 1.925 |
| | 2.820 | 3.015 | 3.168 | 3.243 | 3.247 |
| | 3.339 | 3.346 | 3.359 | 3.367 | 3.376 |
| | 3.400 | 3.406 | 3.424 | 3.440 | 3.446 |
| | 3.486 | 3.490 | 3.523 | 3.534 | 3.580 |
| | 3.596 | 3.604 | 3.618 | 3.634 | 3.722 |
| | 3.771 | 3.783 | 3.811 | 3.927 | 3.942 |
| | 4.152 | 4.182 | 4.205 | 4.215 | 4.222 |
| | 4.246 | 4.265 | 4.288 | 4.314 | 4.360 |
| | 4.426 | 4.492 | 4.514 | 4.559 | 4.603 |
| | 4.623 | 4.668 | 4.691 | | |

The peaks at 3.86, 5.14 and 5.01 ppm in bovine and porcine heparin are not present for salmon GAG. The peaks at 4.12 and 3.99 ppm in bovine and porcine heparin are weak or absent in salmon GAG.

The peaks at 2.8-2.85 and 3.940-3.955 ppm in salmon GAG are absent in porcine and bovine heparin as are the peaks at 3.01, 3.16, 3.24, 3.33, 3.34, 4.28 and 4.31 ppm.

EXAMPLE 8

GAG Extraction from Salmon Intestine 445 g of salmon intestines were mixed with 400 mL water and homogenized. The homogenate was incubated at 80° C. for 1 hour and then rehomogenized. The homogenate was centrifuged at 12,000 rpm for 30 minutes and the solid phase discarded. The pH of the supernatant was adjusted to approx. 8.9 using NaOH and kept at 90° C. for 15 minutes before being centrifuged again as above. This supernatant was applied to a column with the anion exchanger Dowex 2 using a bed volume around 415 mL. The column was washed with 5 mM $NH_4HCO_3$ and the pH adjusted to 8.9 with $NH_3$ and 0.1M NaCl. The column was then washed with the same buffer containing 1.6M NaCl.

Elution was performed using the same buffer containing 2.4M NaCl. The eluate was shown to contain uronic acid using the carbazole test. The eluate from using 1.6M NaCl was also shown to contain uronic acid using the same test.

An aliquot of 10 mL of the GAG eluate using 2.4M NaCl was dialyzed against water, freeze dried, dissolved in 5 mL water and tested for antithrombin accelerating activity:

The test buffer used was 0.1M Tris and HCl to pH 8.4.

0.1 mL thrombin (bovine plasma, Sigma, 5 U/mL in test buffer) was added to 0.3 mL test buffer alone (Run 1) or 0.2 mL test buffer and 0.1 mL water (Run 2) or 0.2 mL test buffer and 0.1 mL antithrombin (Atenativ, Pharmacia & Upjohn, 0.1 mg/mL in test buffer) (Run 3) or 0.1 mL test buffer and 0.1 mL antithrombin (0.1 mL in test buffer) and 0.1 mL dissolved 2.4 M NaCl eluate (Run 4). Each mixture was further mixed with 0.1 mL synthetic substrate (S-2238 from Kabi—0.75 mmol/L in water) and incubated at 37° C. for 2 minutes. The reaction was stopped by adding 0.1 mL of 20 % acetic acid and the amidolytic activity on the substrate was measured by determining the absorbance (A) at 405 nm.

| Results from the 2.4 M NaCl fraction | | |
|---|---|---|
| Run | A, 405 nm | Comments |
| 1 | 1.070 | no GAG |
| 2 | 1.028 | no GAG |
| 3 | 0.761 | thrombin & antithrombin |
| 4 | 0.279 | thrombin & antithrombin & piscine GAG |

An aliquot of 10 mL of the 1.6 M NaCl eluate was dialyzed against water, freeze dried and dissolved in 5 mL water and tested for antithrombin accelerating activity using the solutions and reagents described in run above:

0.2 mL test buffer and 0.1 mL thrombin and 0.1 mL antithrombin (Run 1) or 0.1 mL test buffer and 0.1 mL thrombin and 0.1 mL antithrombin and 0.1 mL dissolved 1.16M NaCl eluate (Run 2). These were each mixed with 0.1 mL synthetic substrate (S-2238 from Kabi—0.75 mmol/L in water) and incubated at 37° C. for 2 minutes. The reaction was stopped by adding 0.1 mL of 20% acetic acid and the amidolytic activity on the substrate was measured by determining the absorbance (A) at 405 nm.

| Results from the 1.6 M NaCl fraction | | |
|---|---|---|
| Run | A, 405 nm | Comments |
| 1 | 0.767 | thrombin & antithrombin |
| 2 | 0.351 | thrombin & antithrombin & piscine GAG |

In both cases, that is from both the 1.6 M NaCl fraction and from the 2.4 M NaCl fraction (runs 2 and 4 respectively) there are anticoagulation effects from piscine GAG.

The invention claimed is:

1. An isolated glucosaminoglycan having high affinity anticoagulant activity obtained from salmon gills or guts, or a salt or derivative thereof, wherein said isolated glucosaminoglycan comprises a pentasaccharide binding site for antithrombin, and wherein said isolated glucosaminoglycan contains at least one pentasaccharide unit having the sequence N-acetylglucosamine-6-O-sulfate, glucoronic acid, N-sulfated glucosamine-3,6-O-disulfate, iduronic acid 2-O-sulfate and N-sulfated glucoamine-6-O-sulfate.

2. An isolated glycosaminoglycan having high affinity anticoagulant activity obtained from salmon, or a salt or derivative thereof, wherein said isolated glycosaminoglycan comprises a pentasaccharide binding site for antithrombin, and wherein said isolated glycosaminoglycan contains at least one pentasaccharide unit having the sequence N-acetylglucosamine-6-O-sulfate, glucoronic acid, N-sulfated glucosamine-3,6-O-disulfate, iduronic acid 2-O-sulfate and N-sulfated glucoamine-6-O-sulfate.

3. An isolated glycosaminoglycan having high affinity anticoagulant activity and extracted from salmon guts, skin, tail or gills, or a salt or derivative thereof, wherein said isolated glycosaminoglycan comprises a pentasaccharide binding site for antithrombin, and wherein said isolated glycosaminoglycan contains at least one pentasaccharide unit having the sequence N-acetylglucosamine-6-O-sulfate, glucoronic acid, N-sulfated glucosamine-3,6-O-disulfate, iduronic acid 2-O-sulfate and N-sulfated glucoamine-6-O-sulfate.

4. The isolated glucosaminoglycan or glycosaminoglycan or salt or derivative thereof as claimed in any one of claims 1, 2 or 3, wherein said isolated glucosaminoglycan or glycosaminoglycan or salt or derivative thereof is in sterile form.

5. The isolated glucosaminoglycan or glycosaminoglycan or salt or derivative thereof as claimed in claim 4, wherein said isolated glucosaminoglycan or glycosaminoglycan or salt or derivative thereof contains no more than 10% by weight of non-glucosaminoglycan biological materials.

6. The isolated glucosaminoglycan or glycosaminoglycan or salt or derivative thereof as claimed in claim 4, wherein said isolated glucosaminoglycan or glycosaminoglycan or salt or derivative thereof contains no more than 2% by weight of non-glucosaminoglycan biological materials.

7. The isolated glucosaminoglycan or glycosaminoglycan or salt or derivative thereof as claimed in claim 6, wherein said isolated glucosaminoglycan or glycosaminoglycan or salt or derivative thereof has a molecular weight in the range 500 to 30,000 Daltons.

8. The isolated glucosaminoglycan or glycosaminoglycan or salt or derivative thereof as claimed in claim 6, wherein said isolated glucosaminoglycan or glycosaminoglycan or salt or derivative thereof has a molecular weight of at least 1000 Daltons.

9. The isolated glucosaminoglycan or glycosaminoglycan or salt or derivative thereof as claimed in claim 6, wherein said isolated glucosaminoglycan or glycosaminoglycan or salt or derivative thereof has a molecular weight of at least 1500 Daltons.

10. A pharmaceutical composition comprising the isolated glucosaminoglycan or glycosaminoglycan or salt or derivative thereof as claimed in claim 9, together with a physiologically tolerable carrier or excipient, and optionally also a therapeutic or prophylactic drug substance.

11. A diagnostic assay kit comprising the isolated glucosaminoglycan or glycosaminoglycan or salt or derivative thereof as claimed in claim 9.

12. A method of reducing blood coagulation in a human or mammalian body which method comprising administering an anticoagulant effective amount of the isolated glucosaminoglycan or glycosaminoglycan or salt or derivative thereof as claimed in claim 9, to a human or mammal in need thereof.

13. The isolated glucosaminoglycan or glycosaminoglycan of claim 1 or 2, wherein said glucosaminoglycan or glycosaminoglycan is produced by a method comprising the following steps:
 (i) homogenizing salmon guts, skin, tail or gills to produce a homogenate;
 (ii) contacting said homogenate, or fraction thereof, with a column coupled to antithrombin;
 (iii) eluting bound glucosaminoglycans or glycosaminoglycans from said column in fractions and determining which fractions contain antithrombin-binding glucosaminoglycan or glycosaminoglycans, and;
 (iv) isolating said antithrombin-binding glucosaminoglycan or glycosaminoglycans.

14. The isolated glycosaminoglycan or salt or derivative thereof as claimed in claim 2, wherein said isolated glycosaminoglycan or salt or derivative thereof is extracted from salmon guts or gills.

15. The isolated or glycosaminoglycan or salt or derivative thereof as claimed in claim 14, wherein said isolated glycosaminoglycan or salt or derivative thereof is extracted from salmon gills.

* * * * *